(12) United States Patent
Jorda et al.

(10) Patent No.: US 6,590,130 B2
(45) Date of Patent: Jul. 8, 2003

(54) PROCESS FOR THE PREPARATION OF 1,1,1-TRIFLUORO-2,2-DICHLOROETHANE

(75) Inventors: Eric Jorda, Lyons (FR); Eric Lacroix, d'Azergues (FR); Sylvain Perdrieux, Charly (FR)

(73) Assignee: Atofina, Paris la Defense Cedex (FR)

( * ) Notice: Subject to any disclaimer, the term of this patent is extended or adjusted under 35 U.S.C. 154(b) by 0 days.

(21) Appl. No.: 09/795,763

(22) Filed: Feb. 28, 2001

(65) Prior Publication Data

US 2002/0198418 A1 Dec. 26, 2002

(30) Foreign Application Priority Data

Feb. 29, 2000 (FR) .......................... 2000 02530

(51) Int. Cl.$^7$ .......................... C07C 17/00; C07C 19/08; C07C 21/18; C07C 23/00; C07C 25/13
(52) U.S. Cl. ........................................ 570/123
(58) Field of Search ........................................ 570/123

(56) References Cited

U.S. PATENT DOCUMENTS 5,723,700 A    3/1998   Lee et al. .................. 570/168

FOREIGN PATENT DOCUMENTS

| EP | 0 346 612 | 12/1989 |
| EP | 0 402 874 | 12/1990 |
| EP | 0 462 514 | 12/1991 |
| EP | 0 583 703 | 2/1994  |
| EP | 0 638 535 | 2/1995  |
| EP | 0 687 660 | 12/1995 |

*Primary Examiner*—Johann Richter
*Assistant Examiner*—Elvis O. Price
(74) *Attorney, Agent, or Firm*—Clifford Chance US LL

(57) ABSTRACT

The invention relates to a process for the preparation of 1,1,1-trifluoro-2,2-dichloroethane (F123).

This process consists in bringing 1,1,1-trifluoro-2-chloroethane (F133a) into contact with chlorine in the presence of hydrogen fluoride and of a fluorination catalyst.

The F133a can be obtained by chlorination of trichloroethylene and the F123 can subsequently be fluorinated to F125.

12 Claims, 2 Drawing Sheets

PROCESS FOR THE PREPARATION OF 1,1,1-TRIFLUORO-2,2-DICHLOROETHANE

A subject-matter of the present invention is a process for the preparation of 1,1,1-trifluoro-2,2-dichloroethane (F123) by catalytic chlorination of 1,1,1-trifluoro-2-chloroethane (F133a) in the presence of hydrogen fluoride (HF). The invention also relates to the application of this process to a process for the manufacture of pentafluoroethane (F125).

As the compounds F123 and F125 can be used as substitutes for perchlorofluorocarbons (CFC) in the field of aerosols (propellants) and in that of refrigeration, there is currently a search for high performance processes for their industrial production.

WO 95/16654 discloses an operation in which F133a is brought into contact at a temperature of 340° C. with chlorine and HF in the presence of a chromium catalyst. Although the conversion of F133a in this reaction is high, it predominantly produces 1,1,1,2-tetrafluoroethane (F134a) at this temperature. Thus, the selectivity of F123 does not exceed 15%, which does not allow production of this compound under industrially acceptable conditions to be envisaged.

WO 94/11327 mentions an operation in which F133a is brought into contact, at temperatures of less than 300° C., with chlorine and HF in the presence of a chromium catalyst. This reaction is carried out with a very large excess of chlorine and of HF and preferably results in the formation of F124 and of F125; thus, the selectivity for F123 remains below 8% and the 110 series/120 series ratio is greater than 10%.

EP-A-526 908 and EP-A-346 612 provide for the preparation of F123 by bringing chlorine into contact with F133a at a temperature preferably lying between 350 and 450° C. in the absence or in the presence of a catalyst, this chlorination being carried out in the absence of HF.

U.S. Pat. No. 4,145,368 provides a process which consists in reacting chlorine with F133a, and then separating the F123 from the reaction mixture, and in reacting the F113a resulting from this separation with a fresh amount of F133a, this reaction being carried out in the vapour phase and preferably between 350 and 425° C. in the present of a catalyst, such as a chromium oxide.

According to this document, the final selectivity for F123 does not exceed 29%.

EP-B-407 990 provides for the chlorination of F133a to F123 by thermal or catalytic activation in the liquid phase under pressure. The selectivity for F123 can range from 67.9 to 83.4%, the reaction pressure ranging from 50 to 127 bar.

EP-A-402 874 provides for the reaction of the chlorine with F133a between 350 and 450° C. in the absence of catalyst and of HF. According to this document, the production of F113a can be eliminated by virtue of a specific combination of conditions relating to temperature, contact time and molar ratio of the reactants.

U.S. Pat. No. 5,414,166 provides for chlorination of F133a in the presence of hydrogen between 250 and 500° C. and preferably between 350 and 450° C.; the selectivity for F123 can range from 65 to 92%.

U.S. Pat. No. 5,723,700 discloses a stage during which F133a, HF and $Cl_2$ react in the presence of a fluorination catalyst between 300 and 450° C. to produce essentially F134a and traces of F123.

The invention provides a process for the preparation of F123 by chlorination of F133a, according to which a relatively moderate temperature is employed.

The invention also provides a process for the preparation of F123 by chlorination of F133a, according to which the pressure employed is atmospheric pressure or a moderate pressure, for example not exceeding 25 bar.

The invention also provides a process for the preparation of F123 by chlorination of F133a, according to which a chlorination and/or fluorination catalyst is present.

The invention also provides a process for the preparation of F123 by chlorination of F133a, according to which a selectivity for F123 of greater than 50% is obtained.

The invention also provides such a process, according to which the selectivity for F123 is greater than 70%.

The invention more specifically provides a process for the preparation of 1,1,1-trifluoro-2,2-dichloroethane (F123) by bringing 1,1,1-trifluoro-2-chloroethane (F133a) into contact with chlorine, the said process being characterized in that the said contacting operation is carried out in the presence of HF and of a catalyst under conditions of temperature and of contact time and with $Cl_2$/F133a and HF/F133a molar ratios such that HF does not substantially react with the F133a and the F123 formed and promotes the selectivity for F123.

The invention relates more particularly to a process such that HF does not substantially react with the F133a and the F123 to give more highly fluorinated derivatives, such as F124 or F134a.

In the implementation of the process according to the invention, it is advisable to choose operating conditions such that HF behaves essentially as diluent and/or stabilizer for the reaction and the reactants and not as reactant in a fluorination reaction. The temperature conditions, the $Cl_2$/F133a and HF/F133a molar ratios and the contact time can generally be chosen within the ranges known for this type of chlorination reaction and such as reported, for example, above with reference to the documents relating to the said chlorination reaction.

Purely by way of illustration and which should not, for this reason, limit the field of the invention, orders of magnitude recommended for the operating conditions in question will be indicated below.

The temperature of the reaction mixture is generally between 150 and 320° C. This temperature is preferably between 250 and 300° C.

The chlorine/F133a molar ratio can be between 0.01 and 0.50 and it is preferably between 0.05 and 0.15.

The HF/133a molar ratio can generally be between 0.5 and 2.5. For practical reasons, related inter alia to the separation of the products for the purpose of the recycling of the unconsumed reactants and of the HF, a ratio between 0.8 and 1.2 is preferably chosen.

The time for contact between F133a, chlorine and HF over the catalyst can be between 5 and 100 seconds; it is recommended to have a contact time of between 10 and 60 seconds. The contact time is calculated here as the ratio of the apparent volume of the catalyst to the total flow rate by volume of the gases fed to the reactor under the reaction pressure and temperature conditions.

The catalysts which can be used for this invention are the chlorination catalysts which are known to a person skilled in the art and which are resistant to hydracids, such as HF and HCl. However, preference is given to catalysts generally used for fluorination reactions with HF. Mention may be made, by way of indication, of bulk or supported catalysts (supported on fluorinated alumina or on charcoal, for example) based on Cr, Zn, Ni or Mg oxide, alone or as a mixture. For this invention, preference will be given to mixed catalysts composed of nickel and chromium oxides, halides and/or oxyhalides deposited on a support composed of aluminium fluoride or of a mixture of aluminium fluoride and of alumina, such as disclosed, for example, in Patents FR 2 669 022 and EP-B-0 609 124.

Prior to the chlorination reaction, the catalyst can be conditioned, if necessary by heat treatment in the presence of $Cl_2$ and/or HF, for example by following the method disclosed in EP-B-0 609 124.

When a mixed nickel/chromium catalyst is used, catalysts comprising, by mass, from 0.5 to 20% of chromium and from 0.5 to 20% of nickel and more particularly those comprising from 2 to 10% by mass of each of these metals in a nickel/chromium atomic ratio of between 0.1 and 5, preferably in the region of 1, will be recommended.

As has been specified, the process in accordance with the invention consists in particular in bringing chlorine into contact with F133a, in the presence of HF and of a catalyst, under conditions such that HF does not substantially react with the F133a and the F123 formed to give more highly fluorinated derivatives. These conditions are advantageously chosen within the temperature, molar ratio and contact time regions indicated above and it would be up to a person skilled in the art to choose the exact conditions of a reaction taking into account the desired result. Thus, from the moment when the temperature parameter will have been chosen, for example 280° C., it can be advantageous to reduce the $Cl_2$/F133a molar ratio, for example around 10%, to obtain the best selectivity for the 120 series at the expense of the 110 series. Likewise, it will be advisable, for a certain temperature and a certain level of chlorine, to choose the contact time making it possible to combine the appropriate degree of conversion of the F133a and good selectivity for F123. Likewise again, the HF/F133a molar ratio can be chosen, for example, according to the desired or acceptable values for the 110 series/120 series molar ratio. As has been indicated, this HF/F133a ratio can generally range from 0.5 to 2.5, taking into account the other reaction conditions (temperature, contact time, $Cl_2$/F133a molar ratio), but this HF/F133a molar ratio is preferably in the vicinity of 1, for example between 0.8 and 1.2.

The preceding directions demonstrate that the values recommended for the operating conditions have an essentially informative role, it being known that it would not be departing from the scope of the invention to use, for one or other of the reaction parameters, values situated above or below the values indicated above, provided that such operating modifications do not involve a reaction of HF with F133a resulting in the formation of substantial amounts of more highly fluorinated derivatives.

The chlorination reaction can be carried out in the gas phase, in a stationary bed or in a fluid bed, batchwise or, preferably, continuously, with a possibility of recycling HF and unconverted reactants to the reactor. The hydrochloric acid formed during the reaction is separated, preferably, before the recycling. The F123 recovered can be purified by distillation according to the desired purity.

The chlorine can be introduced into the reactor pure or diluted in an inert gas, such as nitrogen. The materials used for the construction of the plant must be compatible with the presence of chlorine and of hydracids, such as HCl and HF; they can be chosen, for example, from "Hastelloy" or from "Inconel", which are resistant to corrosive media comprising these hydracids.

The chlorination reaction according to the invention can be carried out at atmospheric pressure or at a pressure greater than the latter. For practical reasons, the reaction is generally carried out in a region ranging from 0 to 25 bar relative and preferably between 0 and 15 bar relative.

Under operating conditions capable of fouling the catalyst, it may be prudent to introduce oxygen at a low content with the reactants. This content can vary, according to the operating conditions, between 0.02 and 5% with respect to the organic reactants (molar percentage). The oxygen can be introduced continuously or sequentially.

The process in accordance with the invention makes it possible to prepare F123 from F133a under moderate temperature and pressure conditions and with an excellent selectivity for F123.

The starting 1,1,1-trifluoro-2-chloroethane (F133a) can itself be obtained by application of processes which are now well known. F133a can in particular be prepared by fluorination of trichloroethylene (for example by following the method 10 recommended by McBee et al., Ind. Eng. Chem., 39, 409–412), by fluorination of F132b, F130a or F1122, or by hydrogenolysis of F113a.

In the invention, preference is given to F133a obtained by fluorination of trichloroethylene.

Another subject-matter of the invention is therefore a process for the preparation of F123 from trifluoroethylene, the said process comprising:
  a) a stage of fluorination of trichloroethylene in a reaction, in the liquid phase or gas phase, in the presence of a catalyst and under a pressure resulting, after separation of HCl and heavy products, in a mixture of F133a accompanied by HF entrained in the azeotropic form;
  b) a stage of chlorination of F133a by bringing the said F133a into contact with chlorine in the presence of HF and of a catalyst under temperature and contact time conditions and with $Cl_2$/F133a and HF/F133a ratios such that HF does not substantially react with the F133a and the F123 formed.

In phase a), for a liquid-phase process, use is preferably made of a catalyst based on antimony salts and the reaction is advantageously carried out under a pressure of at least 10 bar absolute. Trichloroethylene can also be reacted with HF in the presence of chromium oxide or of chromium oxyfluoride in a gas-phase process.

The F123 can be used as it is, for example as propellant, in refrigeration and in the manufacture of foams, where it advantageously replaces F11 because of its harmlessness with regard to the ozone in the stratosphere. For this reason, the process in accordance with the invention, which, by the results to which it leads, can be operated on an industrial level, is particularly advantageous, both starting from trichloroethylene and from F133a.

The F123 can also be subjected to an additional fluorination and can thus result in F125 (pentafluoroethane). This reaction can be carried out according to various processes which are now known: this stage generally comprises bringing F123 (alone or as a mixture with other compounds of the 120 series) into contact with HF in the presence of a fluorination catalyst, to obtain F125.

This stage can be carried out in the vapor phase and the catalyst can be chosen from the catalysts whose use is disclosed, for example, in EP-B-609 124 or in the references to which this patent refers, the said patent being incorporated here in particular for the conditions recommended for this reaction.

A further subject-matter of the invention is thus a process for the preparation of pentafluoroethane (F125), the said process comprising:
  a) a stage of fluorination of trichloroethylene as described above and resulting in particular in F133a;
  b) a stage of chlorination of F133a as described above and resulting in particular in F123;
  c) a stage of fluorination of F123 by bringing F123 into contact with HF in the presence of a catalyst, with or without recycling of F124, it being possible for the fluorination of F124 to form the subject of a separate stage.

In this stage, the catalyst is advantageously a mixed catalyst composed of nickel and chromium oxides, halides and/or oxyhalides, as disclosed in EP-B-609 124. It is also possible to use catalysts based on chromium oxide or oxyfluoride or based on alumina or on aluminium fluoride, optionally doped with a metal, such as zinc, nickel or iron. Such catalysts are disclosed, for example, in EP-502 605 or WO 93/16798. Use may also be made of a catalyst of the chromium/charcoal type, such as disclosed, for example, in EP-A-456 552.

For this stage, use is preferably made of a mixed catalyst described above deposited on a support composed of aluminium fluoride or of a mixture of aluminium fluoride and of alumina.

The temperature of this fluorination reaction can be between 250 and 470° C. and is preferably between 280 and 410° C. The time for contact between HF and F123 can be between 3 and 100 s, preferably between 5 and 30 s. The HF/F123 molar ratio can range from 1/1 to 20/1 and preferably from 2/1 to 9/1.

Although the reaction can be carried out at atmospheric pressure, it is preferable to carry out the reaction under a slight pressure, for example not exceeding 10 bar absolute and even less than 5 bar absolute.

The F125 obtained can subsequently be purified, for example by application of the methods disclosed in FR-2 758 137 or WO 95/21147, the contents of which are incorporated here by reference.

The process for the preparation of F125 from trichloroethylene, which also constitutes a subject-matter of the invention, can be carried out continuously in a plant such as presented diagrammatically in one or other of the appended figures.

BRIEF DESCRIPTION OF THE DRAWINGS

These figures illustrate a general diagram of the three stages I, II and III of the process in question.

The plant comprises in particular (see FIG. 1):

Figure 1:
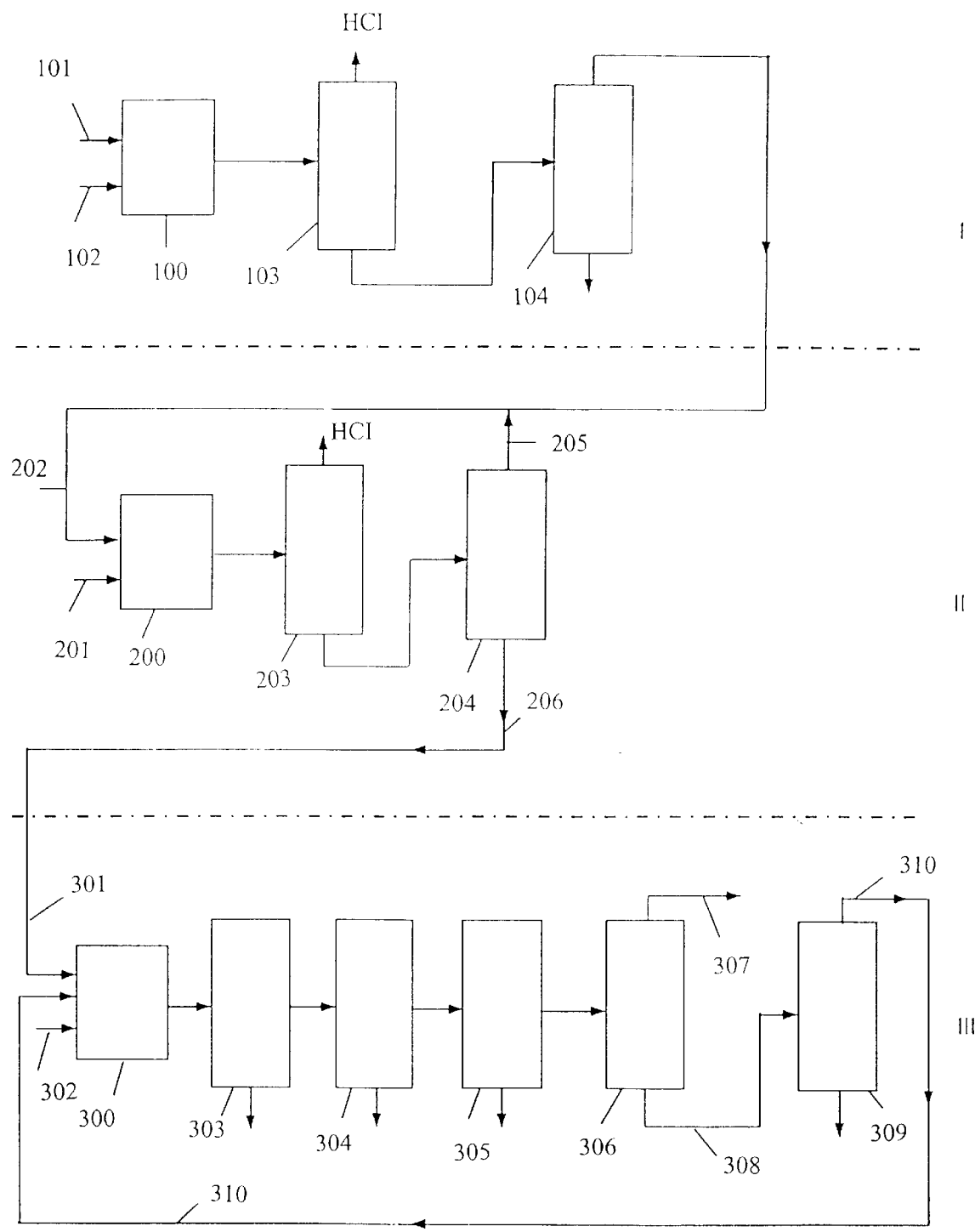

Stage I
  a reactor (100) comprising the catalyst;
  trichloroethylene (101) and HF (102) inlets;
  an HCl distillation column (103);
  a column for separation of F133a+HF from the heavy products (104);

Stage II
  a chlorination reactor (200) fed with
  F133a and HF (202);
  chlorine (201);
  an HCl separation column (203);
  a column (204) for separation of crude F123 (206) from unreacted F133a (+ in particular azeotropic HF+unreacted Cl$_2$), which are recycled (205);

Stage III
  a fluorination reactor (300), fed with crude F123 (206/301) originating from the column (204) of the preceding stage, with HF (302) and optionally with crude F124 (310) recycled from the column (309);
  at the outlet of the reactor (300), devices for treating the reaction gases (columns 303, 304 and 305) intended to recover the HCl reaction by-product and the unconverted HF and to neutralize the fluorocarbon compounds before their distillation;
  a column (306) which makes it possible subsequently to extract the F125 (307) at the top, the bottoms (308) subsequently being distilled on the column (309) in order to obtain an F124+F123 mixture (310) purified from its content of heavy products, the said mixture subsequently being recycled to the reactor (300) in order to be fluorinated therein to F125.

Figure 2:
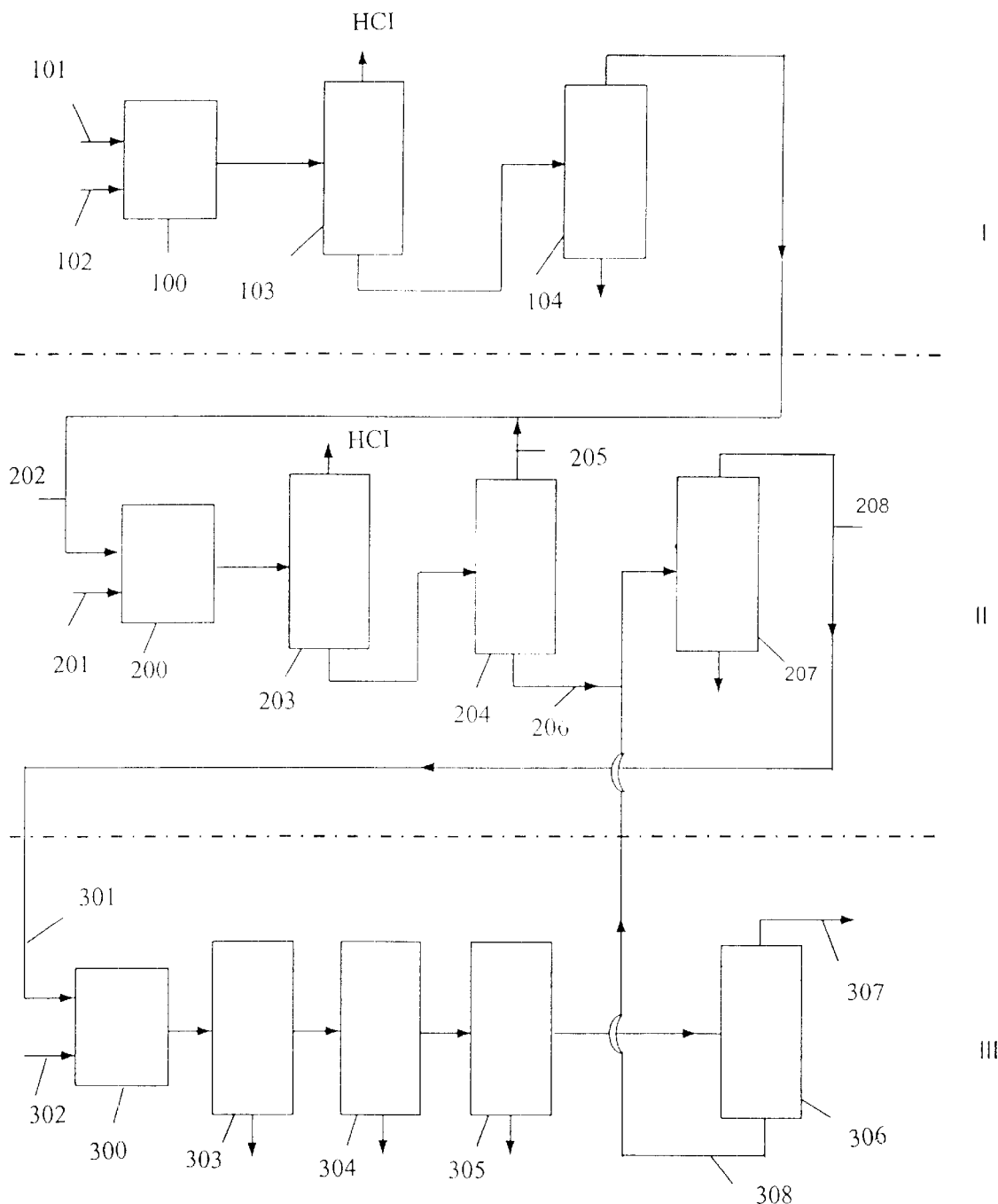

An advantageous alternative form of this diagram is represented in FIG. 2, in which a column (207) makes it possible to purify both the crude F123 (206) resulting from the column (204) of Stage II and the crude F124+F123 mixture resulting from the bottom of the column (306) of Stage III: in this alternative form, which makes it possible to feed the reactor (300) with cleaner products, there is no longer any reason for the column (309) to exist.

Of course, the industrial plant comprises additional devices with known uses (bleed, evaporators, superheater, decanters).

The invention thus also relates to a plant for the production of F125 from trichloroethylene which comprises at least the sequence of devices as represented in the figure.

The invention will now be illustrated by the following examples, which are only given purely by way of indication.

EXAMPLE 1

75 cm$^3$ of Ni—Cr/AlF$_3$ catalyst (prepared as disclosed in Patent FR 2 669 022) are introduced into an Inconel tube with an internal diameter of 21 mm. The catalyst is treated for 15 h with 1 mol/h of anhydrous HF at 350° C. and at atmospheric pressure. Prior to the reaction, the HF flow rate is adjusted to 1.13 mol/h and the temperature to 280° C. A Cl$_2$/N$_2$ mixture comprising 15 molar % of chlorine is subsequently introduced into the reactor with a flow rate of 0.79 mol/h. Finally, CF$_3$—CH$_2$Cl is introduced into the reactor with a flow rate of 102 mol/h and the total reaction pressure is regulated at 15 bar. After reacting for 6 h, a gas sample is withdrawn for analysis by gas chromatography. Before making the withdrawal, the gas is freed from HF, HCl and chlorine by bubbling into wash bottles comprising water and sodium hydroxide/sulphite and then dried over CaCl$_2$.

The conversion of F133a is 7% for a selectivity for F123 of 93%. The 110 series/120 series ratio is 3.4%.

EXAMPLES 2 to 7

Following the same protocol as in Example 1, various conditions were tested:

| Conditions | Ex. 2 | Ex. 3 | Ex. 4 | Ex. 5 | Ex. 6 | Ex. 7 |
|---|---|---|---|---|---|---|
| Temperature (° C.) | 280 | 280 | 280 | 310 | 280 | 280 |
| Cl$_2$/F133a MR | 0.13 | 0.47 | 0.13 | 0.14 | 0.1 | 0.1 |
| HF/F133a MR | 2 | 2.3 | 2.1 | 2.1 | 1 | 0.7 |
| ct (s) | 20 | 13 | 38 | 19 | 15 | 32 |
| Results | | | | | | |
| F133a conversion, % | 6.2 | 13.3 | 10.1 | 12.2 | 4.3 | 10 |
| F123 selectivity, % | 93 | 87 | 93 | 85 | 93 | 74 |
| 110 series/120 series ratio | 2.8% | 7.8% | 4% | 5% | 1.8% | 6.4% |

Comparative Examples

Example 1a (Without HF)

75 cm$^3$ of Ni—Cr/AlF$_3$ catalyst (prepared as disclosed in Patent FR 2 669 022) are introduced into an Inconel tube with an internal diameter of 21 mm. The catalyst is treated for 15 h with 1 mol/h of anhydrous HF at 350° C. and atmospheric pressure. Prior to the reaction, the HF flow is halted and the temperature reduced to 280° C. A $Cl_2/N_2$ mixture comprising 15 molar % of chlorine is subsequently introduced into the reactor with a flow rate of 1.13 mol/h. Finally, $CF_3$—$CH_2Cl$ is introduced into the reactor with a flow rate of 1.63 mol/h and the total reaction pressure is regulated at 15 bar. After reacting for 6 h, a gas sample is withdrawn for analysis by gas chromatography. Before making the withdrawal, the gas is freed from HF, HCl and chlorine by bubbling into wash bottles comprising water and sodium hydroxide/sulphite and then dried over $CaCl_2$.

The conversion of F133a is 10%, for a selectivity for F123 of 42%. The 110 series/120 series ratio is 37%.

Example 1b Without HF and Without Catalyst

A $Cl_2/N_2$ mixture comprising 15 molar % of chlorine is introduced, with a flow rate of 1.3 mol/h, into an empty Inconel tube with an internal diameter of 21 mm. $CF_3$—$CH_2Cl$ is subsequently introduced into the reactor with a flow rate of 2.08 mol/h and the total reaction pressure is regulated at 15 bar.

After reacting for 6 h, a gas sample is withdrawn for analysis by gas chromatography. Before making the withdrawal, the gas is freed from HF, HCl and chlorine by bubbling into wash bottles comprising water and sodium hydroxide/sulphite and then dried over $CaCl_2$.

The conversion of F133a is 2% for a selectivity for F123 of 79%. The 110 series/120 series ratio is 15.4%.

What is claimed is:

1. A process for the preparation of 1, 1, 1-trifluoro-2,2-dichloroethane by contacting 1, 1, 1-trifluoro-2-chloroethane with chlorine in the presence of hydrogen fluoride and a mixed catalyst comprising nickel and a chromium oxide, halide, and/or oxyhalide on a support comprising aluminum fluoride or a mixture of aluminum fluoride and alumina at a temperature between 250° C. and 300° C. for a contact time between 10 and 60 seconds, with the chlorine to the 1, 1, 1-trifluoro-2-chloroethane molar ratio being between 0.05 and 0.15 and the hydrogen fluoride to the 1, 1, 1-trifluoro-2-chloroethane molar ratio being between 0.8 and 1.2.

2. A process for the preparation of 1, 1, 1-trifluoro-2,2-dichloroethane by contacting 1, 1, 1-trifluoro-2-chloroethane with chorine in the presence of hydrogen fluoride and a mixed catalyst comprising nickel and a chromium oxide, halide, and/or oxyhalide at a temperature between 150° C. and 320° C. for a contact time between 5 and 100 seconds, with the chlorine to 1, 1, 1,-trifluoro-2-chloroethane molar ratio being between 0.01 and 0.50 and the hydrogen fluoride to 1,1,1-trifluoro-2-chloroethane molar ratio being between 0.5 and 2.5.

3. The process according to claim 2, wherein the temperature is between 250° C. and 300° C.

4. The process according to claim 2, wherein the chlorine to 1,1,1-trifluoro-2-chloroethane molar ratio is between 0.05 and 0.15.

5. The process according to claim 2, wherein the hydrogen fluoride to 1, 1, 1-trifluoro-2-chloroethane molar ratio is between 0.8 and 1.2.

6. The process according to claim 2, wherein the contact time is between 10 and 60 seconds.

7. The process according to claim 2, wherein the mixed catalyst is deposited on a support comprising aluminum fluoride or a mixture of aluminum fluoride and alumina.

8. The process according to claim 2, wherein the temperature is between 250° C. and 300° C., wherein the chlorine to 1, 1, 1-trifluoro-2-chloroethane molar ratio is between 0.05 and 0.15, wherein the hydrogen fluoride to 1, 1, 1-trifluoro-2-chloroethane molar ratio is between 0.8 and 1.2, and wherein the contact time is between 10 and 60 seconds.

9. The process according to claim 1 or 2, characterized in that the process is carried out continuously.

10. The process according to claim 8, characterized in that the process is carried out continuously.

11. The process according to claim 1 or 2, wherein the 1, 1, 1-trifluoro-2,2-dichloroethane is obtained by fluorination of trichloroethylene.

12. The process according to claims 8 or 10, wherein the 1, 1, 1-trifluoro-2,2-dichlorethane is obtained by fluorination of trichloroethylene.

* * * * *